(12) United States Patent
Kapadia

(10) Patent No.: US 11,628,024 B2
(45) Date of Patent: Apr. 18, 2023

(54) SURGICAL ROBOTIC SYSTEMS

(71) Applicant: Covidien LP, Mansfield, MA (US)

(72) Inventor: Jaimeen Kapadia, Cambridge, MA (US)

(73) Assignee: COVIDIEN LP, Mansfield, MA (US)

( * ) Notice: Subject to any disclaimer, the term of this patent is extended or adjusted under 35 U.S.C. 154(b) by 49 days.

(21) Appl. No.: 16/977,504

(22) PCT Filed: Feb. 21, 2019

(86) PCT No.: PCT/US2019/018859
§ 371 (c)(1),
(2) Date: Sep. 2, 2020

(87) PCT Pub. No.: WO2019/173056
PCT Pub. Date: Sep. 12, 2019

(65) Prior Publication Data
US 2021/0052337 A1    Feb. 25, 2021

Related U.S. Application Data

(60) Provisional application No. 62/640,149, filed on Mar. 8, 2018.

(51) Int. Cl.
*A61B 34/30* (2016.01)
*A61B 17/072* (2006.01)
*A61B 17/00* (2006.01)

(52) U.S. Cl.
CPC ........ *A61B 34/30* (2016.02); *A61B 17/07207* (2013.01); *A61B 2017/00398* (2013.01);
(Continued)

(58) Field of Classification Search
CPC .............. A61B 34/30; A61B 2034/305; A61B 2017/00398; A61B 2017/00477; A61B 2017/07285
See application file for complete search history.

(56) References Cited

U.S. PATENT DOCUMENTS

| 5,792,135 A | * | 8/1998 | Madhani ................ A61B 34/77 606/1 |
| 6,132,368 A | | 10/2000 | Cooper |

(Continued)

FOREIGN PATENT DOCUMENTS

| JP | 2013526337 A | 6/2013 |
| WO | 2016043845 A1 | 3/2016 |

(Continued)

OTHER PUBLICATIONS

International Search Report dated Jun. 3, 2019, issued in corresponding International Appln. No PCT/US2019/018859, 3 pages.

(Continued)

*Primary Examiner* — Daniel Jeremy Leeds
(74) *Attorney, Agent, or Firm* — Carter, DeLuca & Farrell, LLP

(57) ABSTRACT

A surgical robotic system includes a robotic arm, an elongated slide coupled to the robotic arm, and an instrument drive unit coupled to a track defined by the slide. The instrument drive unit is configured to move along the track and includes a motor configured to interface with an electromechanical instrument to actuate functions of the electromechanical instrument. The slide is configured to rotate relative to the robotic arm about a longitudinal axis defined by the instrument drive unit.

20 Claims, 8 Drawing Sheets

(52) U.S. Cl.
CPC .............. *A61B 2017/00477* (2013.01); *A61B 2017/07285* (2013.01)

(56) References Cited

U.S. PATENT DOCUMENTS

| | | |
|---|---|---|
| 6,206,903 B1 | 3/2001 | Ramans |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez et al. |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |

(56) References Cited

U.S. PATENT DOCUMENTS

| | | |
|---|---|---|
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,758,313 B2 * | 9/2020 | Bernstein ............... A61B 90/11 |
| 10,828,115 B2 * | 11/2020 | Koenig ................... B25J 9/104 |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |

(56) References Cited

U.S. PATENT DOCUMENTS

| | | |
|---|---|---|
| 10,932,873 B2 | 3/2021 | Griffiths et al. |
| 10,932,877 B2 | 3/2021 | Devengenzo et al. |
| 2007/0089557 A1* | 4/2007 | Solomon ............... B25J 18/007 74/490.01 |
| 2015/0305815 A1 | 10/2015 | Holop et al. |
| 2016/0000512 A1 | 1/2016 | Gombert et al. |
| 2018/0116741 A1* | 5/2018 | Garcia Kilroy ....... G01L 3/1428 |

FOREIGN PATENT DOCUMENTS

| | | |
|---|---|---|
| WO | 2016205481 A1 | 12/2016 |
| WO | 2016209769 A1 | 12/2016 |
| WO | 2017142738 A1 | 8/2017 |
| WO | 2017151873 A1 | 9/2017 |
| WO | 2018001742 A1 | 1/2018 |
| WO | 2019173056 A1 | 9/2019 |

OTHER PUBLICATIONS

Written Opinion of the International Searching Authority dated Jun. 3, 2019, issued in corresponding International Appln. No. PCT/US2019/018859, 4 pages.

International Preliminary Report on Patentability dated Sep. 8, 2020, issued in corresponding International Appln. No. PCT/US2019/018859, 5 pages.

Australian Examination Report dated Oct. 14, 2020, issued in corresponding Australian Appln. No. 2019232675, 3 pages.

Extended European Search Report dated Nov. 10, 2021, issued in corresponding EP Appln. No. 19763458, 9 pages.

Australian Office Action dated Feb. 18, 2022, issued in corresponding AU Appln. No. 2020260417, 4 pages.

Australian Office Action dated Mar. 28, 2022, issued in corresponding Australian Appln. No. 2020260417, 3 pages.

Japanese Office Action dated Mar. 22, 2022, issued in corresponding JP Appln. No. 2020543136, 5 pages.

* cited by examiner

SURGICAL ROBOTIC SYSTEMS

CROSS-REFERENCE TO RELATED APPLICATIONS

This application is a U.S. National Stage Application filed under 35 U.S.C. § 371(a) of International Patent Application Serial No. PCT/US2019/018859, filed Feb. 21, 2019, which claims the benefit of and priority to U.S. Provisional Patent Application Ser. No. 62/640,149, filed Mar. 8, 2018, the entire disclosure of which is incorporated by reference herein.

BACKGROUND

Surgical robotic systems have been used in minimally invasive medical procedures. Some surgical robotic systems included a console supporting a surgical robotic arm and a surgical instrument having at least one end effector (e.g., forceps or a grasping tool) mounted to the robotic arm. The robotic arm provided mechanical power to the surgical instrument for its operation and movement.

Manually-operated surgical instruments often included a handle assembly for actuating the functions of the surgical instrument. However, when using a robotic surgical system, no handle assembly was typically present to actuate the functions of the end effector. Accordingly, to use each unique surgical instrument with a robotic surgical system, an instrument drive unit was used to interface with the selected surgical instrument to drive operations of the surgical instrument.

The instrument drive unit was typically coupled to the robotic arm via a slide. The slide allowed the instrument drive unit and the attached surgical instrument to move along an axis of the slide, providing a means for adjusting the axial position of the end effector of the surgical instrument.

SUMMARY

In accordance with an aspect of the present disclosure, a surgical robotic system is provided and includes a robotic arm, an elongated slide, and an instrument drive unit. The slide is coupled to the robotic arm and defines a track. The instrument drive unit is coupled to the track and is configured to move along the track. The instrument drive unit includes a motor configured to interface with an electromechanical instrument to actuate functions of the electromechanical instrument. The slide is configured to rotate relative to the robotic arm about a longitudinal axis defined by the instrument drive unit.

In aspects of the present disclosure, the motor may have a coupler for interfacing with a corresponding coupler of the electromechanical surgical instrument. The coupler may be disposed adjacent a proximal end of the instrument drive unit.

In aspects of the present disclosure, the instrument drive unit may further include a housing slidably coupled to the track of the slide. The housing may have the motor disposed therein.

In aspects of the present disclosure, the coupler may be disposed within a proximal end of the housing. In aspects, the coupler may be a gear.

In aspects of the present disclosure, the housing may define an elongated channel along its length. The channel may be dimensioned for receipt of a shaft of the electromechanical instrument. The channel may be coaxial with the longitudinal axis of the instrument drive unit.

In aspects of the present disclosure, the housing may have a proximal end configured to support thereon a body portion of the electromechanical instrument.

In aspects of the present disclosure, the proximal end of the housing may be configured to non-rotatably support the electromechanical instrument.

In aspects of the present disclosure, the instrument drive unit may rotate relative to the robotic arm with a rotation of the slide.

In aspects of the present disclosure, the surgical robotic system may further include a coupling member attached to an end portion of the robotic arm. The coupling member may rotatably support the slide thereon. The coupling member may include a cannula configured for receipt of a shaft of the electromechanical instrument. The longitudinal axis about which the slide is configured to rotate may be coaxial with the cannula.

In aspects of the present disclosure, the robotic surgical system may further include an electro-mechanical actuator coupled to the slide and configured to rotate the slide about the longitudinal axis of the instrument drive unit. The electro-mechanical actuator may include a drive motor and a gear driven by the drive motor. The gear may be operably coupled to the slide, such that actuation of the drive motor effects a rotation of the slide.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
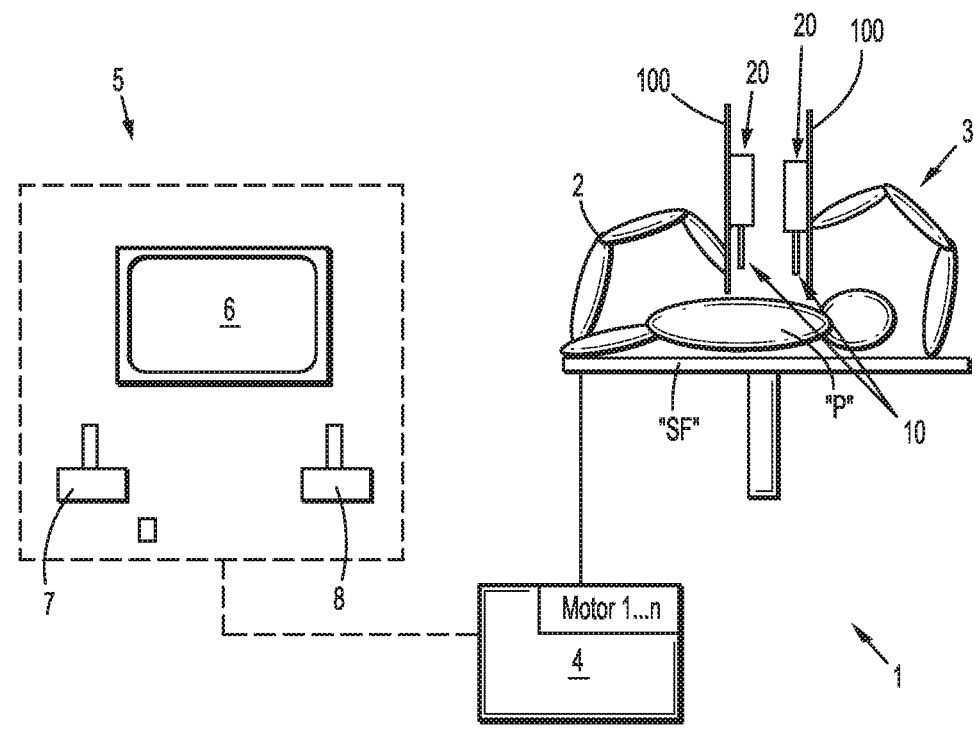
FIG. 1 is a schematic illustration of a surgical robotic system including an instrument drive unit coupled to a slide in accordance with the present disclosure.

Embodiments of the presently disclosed surgical robotic system and methods of use thereof are described in detail with reference to the drawings, in which like reference numerals designate identical or corresponding elements in each of the several views. As used herein, the term "distal" refers to that portion of the surgical robotic system or component thereof that is closest to the patient, while the term "proximal" refers to that portion of the surgical robotic system or component thereof further from the patient.

As will be described in detail below, provided is a surgical robotic system including a robotic arm, an elongated slide or rail coupled to the robotic arm, and an instrument drive unit configured to drive an operation of an attached surgical instrument. The slide defines a track along which the instrument drive unit is axially movable. The slide is coupled to the robotic arm, such that the slide and the attached instrument drive unit are rotatable about a longitudinal axis defined by the slide. The instrument drive unit is configured to allow for a top-loading of the surgical instrument.

Referring initially to FIG. 1, a surgical system, such as, for example, a surgical robotic system 1, generally includes a plurality of surgical robotic arms 2, 3 having an instrument drive unit 20 and an electromechanical instrument 10 removably attached thereto; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached instrument drive units 20, and thus electromechanical instrument 10 execute a desired movement according to a movement defined by means of manual input devices 7, 8. Control device 4 may also be set up in such a way that it regulates the movement of robotic arms 2, 3 and/or of the drives.

Surgical robotic system 1 is configured for use on a patient "P" lying on a surgical table "ST" to be treated in a minimally invasive manner by means of a surgical instrument, e.g., electromechanical instrument 10. Surgical robotic system 1 may also include more than two robotic arms 2, 3, the additional robotic arms likewise being connected to control device 4 and being telemanipulatable by means of operating console 5. A surgical instrument, for example, an electromechanical surgical instrument 10 (including an electromechanical end effector (not shown)), may also be attached to the additional robotic arm.

Figure 3:
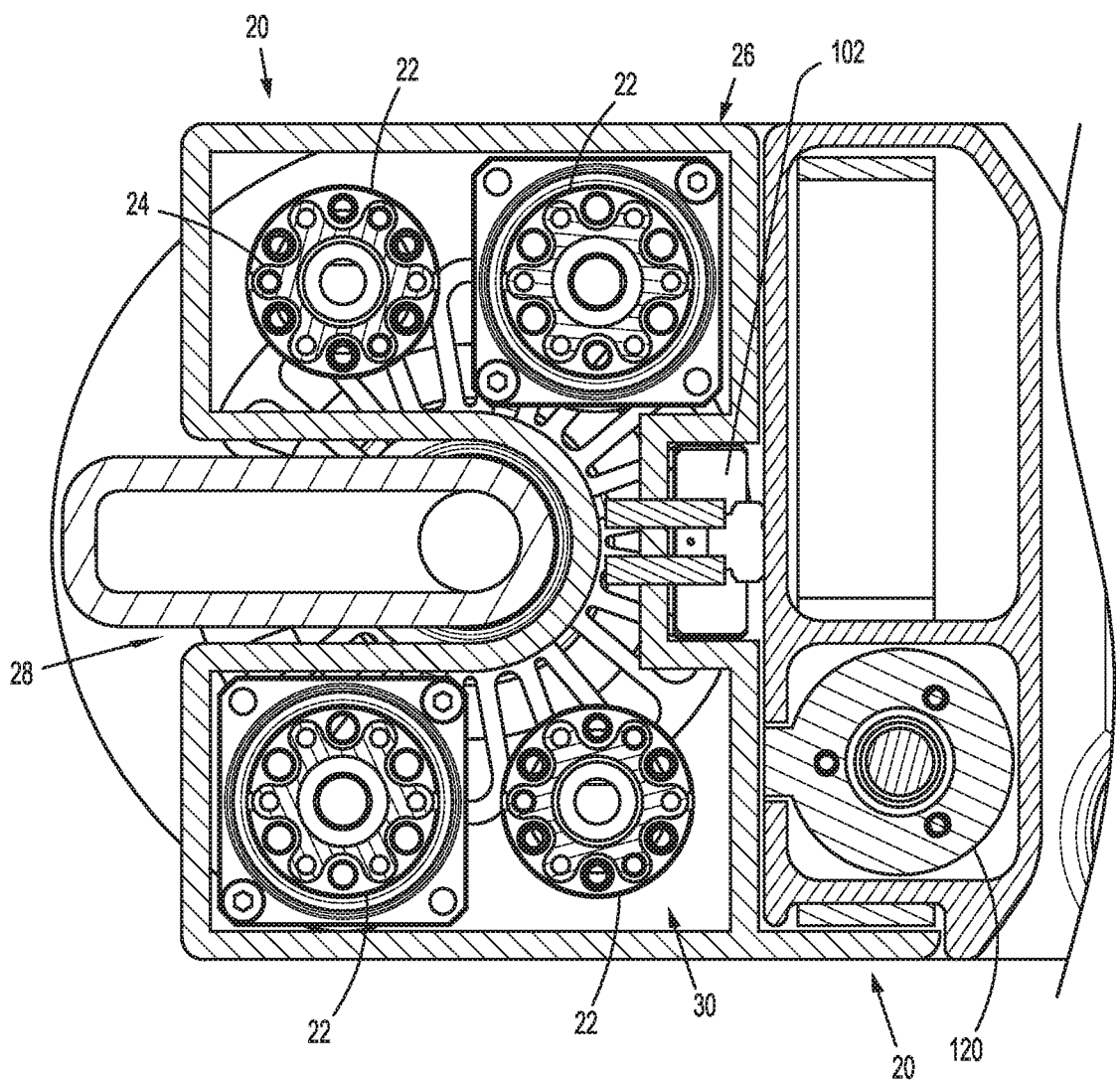
FIG. 3 is a cross-section, taken alone line 3-3 in FIG. 2, of the instrument drive unit and the slide.

Control device 4 may control a plurality of motors, e.g., motors (Motor 1 . . . n), with each motor configured to drive movement of robotic arms 2, 3 in a plurality of directions. Further, control device 4 may control a plurality of motors 22 (FIG. 3) of instrument drive unit 20 to drive various operations of surgical instrument 10, and may control a rotation of an electromechanical actuator 122 (FIG. 5) to rotate a slide 100 about a longitudinal axis "X" of the instrument drive unit 20 (as indicated by arrow "B" of FIG. 4A), as will be described in detail below. The instrument drive unit 20 transfers power and actuation forces from its motors to driven members (not shown) of the electromechanical instrument 10 to ultimately drive movement of components of the end effector (not shown) of the electromechanical instrument 10, for example, a movement of a knife blade (not shown) and/or a closing and opening of jaw members (not shown) of the end effector.

For a detailed description of the construction and operation of a robotic surgical system, reference may be made to U.S. Pat. No. 8,828,023, entitled "Medical Workstation," the entire contents of which are incorporated by reference herein.

With reference to FIGS. 2-4B, the instrument drive unit 20 further includes an outer housing 26 having the plurality of drive motors 22 operably disposed therein. The housing 26 of the instrument drive unit 20 is configured to be slidably coupled to a linear track 102 defined longitudinally along the slide 100. The housing 26 may have a rectangular block shape. In embodiments, the housing 26 may assume any suitable shape, such as, for example, cylindrical. The housing 26 has a proximal end 26a and a distal end 26b. The proximal end 26a of the housing 26 is configured to support thereon a housing or main body portion 12 of the electromechanical instrument 10. In some embodiments, the proximal end 26a of the housing 26 may have a substantially planar proximal surface 34 configured to support the main body portion 12 of the electromechanical instrument 10 thereon.

The housing 26 of the instrument drive unit 20 defines an elongated channel 28 that extends from the proximal end 26a to the distal end 26b thereof. The channel 28 may have a U-shaped profile and be dimensioned for slidable receipt of a shaft 14 of the electromechanical surgical instrument 10. In some embodiments, the channel 28 may be dimensioned to capture the shaft 14 of the electromechanical instrument 10 therein. The housing 26 defines an inner chamber 30 in which the drive motors 22 are disposed.

The drive motors 22 of the instrument drive unit 20 include respective couplers 24 (e.g., gears) disposed at proximal ends thereof. In embodiments, the couplers 24 may be any suitable force-transfer mechanism, such as any suitable screw drive. The couplers 24 are disposed adjacent the proximal end 26a of the housing 26. In embodiments, the couplers 24 may be disposed within the inner chamber 30 of the housing 26 or protrude proximally from the proximal end 26a of the housing 26. The couplers 24 are configured to interface with a corresponding gear or mating coupler (not explicitly shown) disposed in a distal end of the main body portion 12 of the electromechanical instrument 10. Accordingly, upon top loading of the electromechanical instrument 10 into the instrument drive unit 20, the couplers 24 of the instrument drive unit 20 operably couple to the gears/couplers in the distal end of the housing 12 of the electromechanical instrument 10, such that an actuation of the drive motors 22 of the instrument drive unit 20 effects an operation of the electromechanical instrument 10. The couplers 24 may be axially movable relative to the drive motors 22, such that upon the gears/couplers in the distal end of the housing 12 of the electromechanical instrument 10 engaging the couplers 24, the couplers 24 move distally to accommodate a mismatch in clocking when adjacent assemblies are brought into contact with one another. In some embodiments, each drive motor 22 may include a torque sensor.

In embodiments, each drive motor 22 may be configured to actuate a drive rod or a lever arm to effect operation and/or movement of each electromechanical end effector (not shown) of the electromechanical instrument 10. In some embodiments, the drive motors 22 of the instrument drive unit 20 may be used to drive a lead screw (not explicitly shown) of the electromechanical surgical instrument 10.

The main body portion 12 of the electromechanical instrument 10 may have a substantially planar distal surface 16 configured to be supported on the proximal surface 34 of the housing 26 of the instrument drive unit 20. The electromechanical instrument 10 may include a substantially planar, elongated fin 18 extending distally from the distal surface 16 of the main body portion 12 of the electromechanical instrument 10. The fin 18 is dimensioned for receipt in the channel 28 of the housing 26 of the instrument drive unit 20. Upon receipt of the fin 18 of the electromechanical instrument 10 in the channel 28 of the housing 26 of the instrument drive unit 20, a rotation of the instrument drive unit 20 causes the electromechanical instrument 10 to rotate therewith. The shaft 14 of the electromechanical instrument 10 extends distally from and/or through the fin 18 of the electromechanical instrument 10.

Figure 4A:
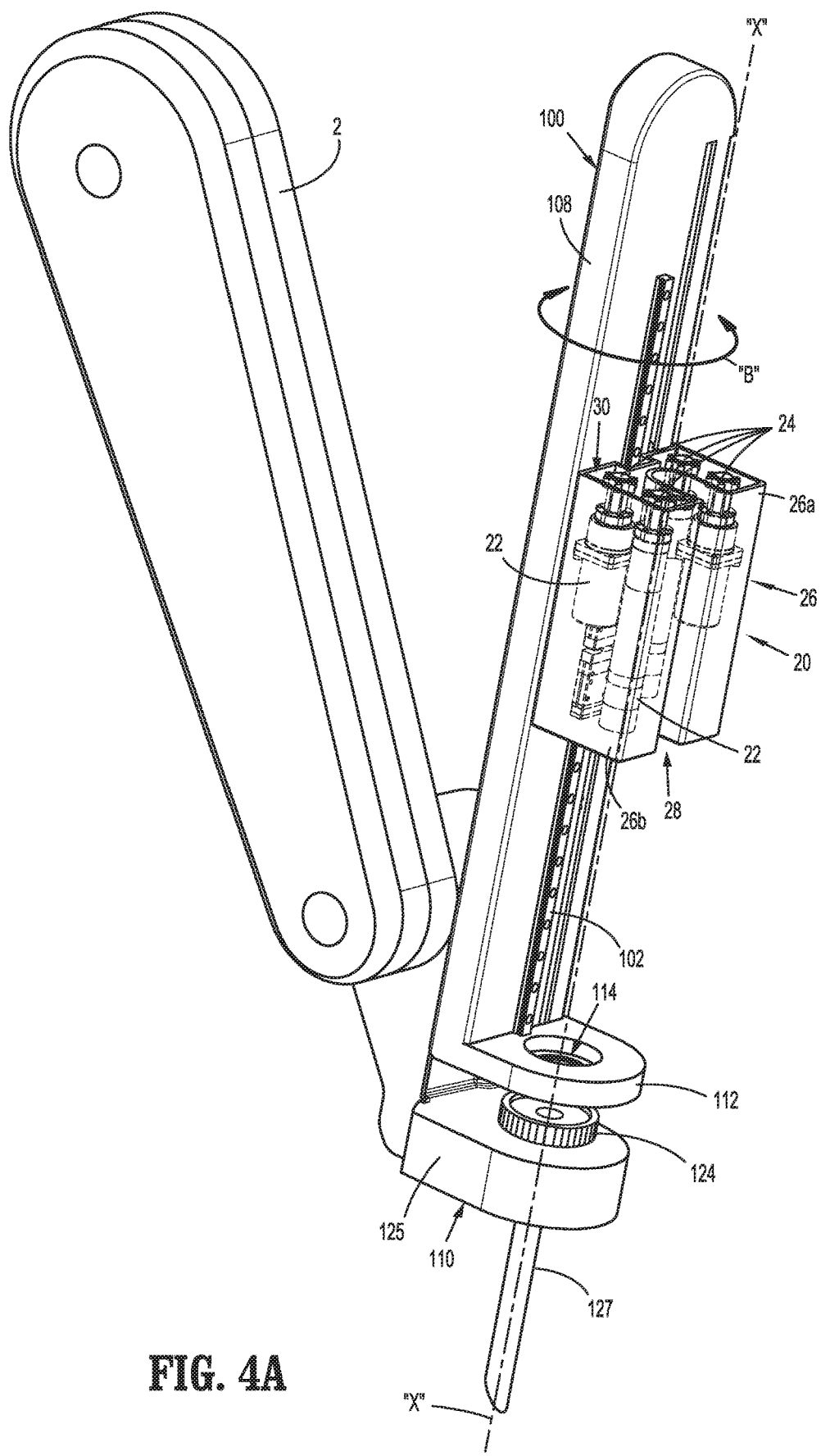
FIG. 4A is a perspective view of a first side of the slide coupled to a surgical robotic arm of the surgical robotic system.
Figure 4B:
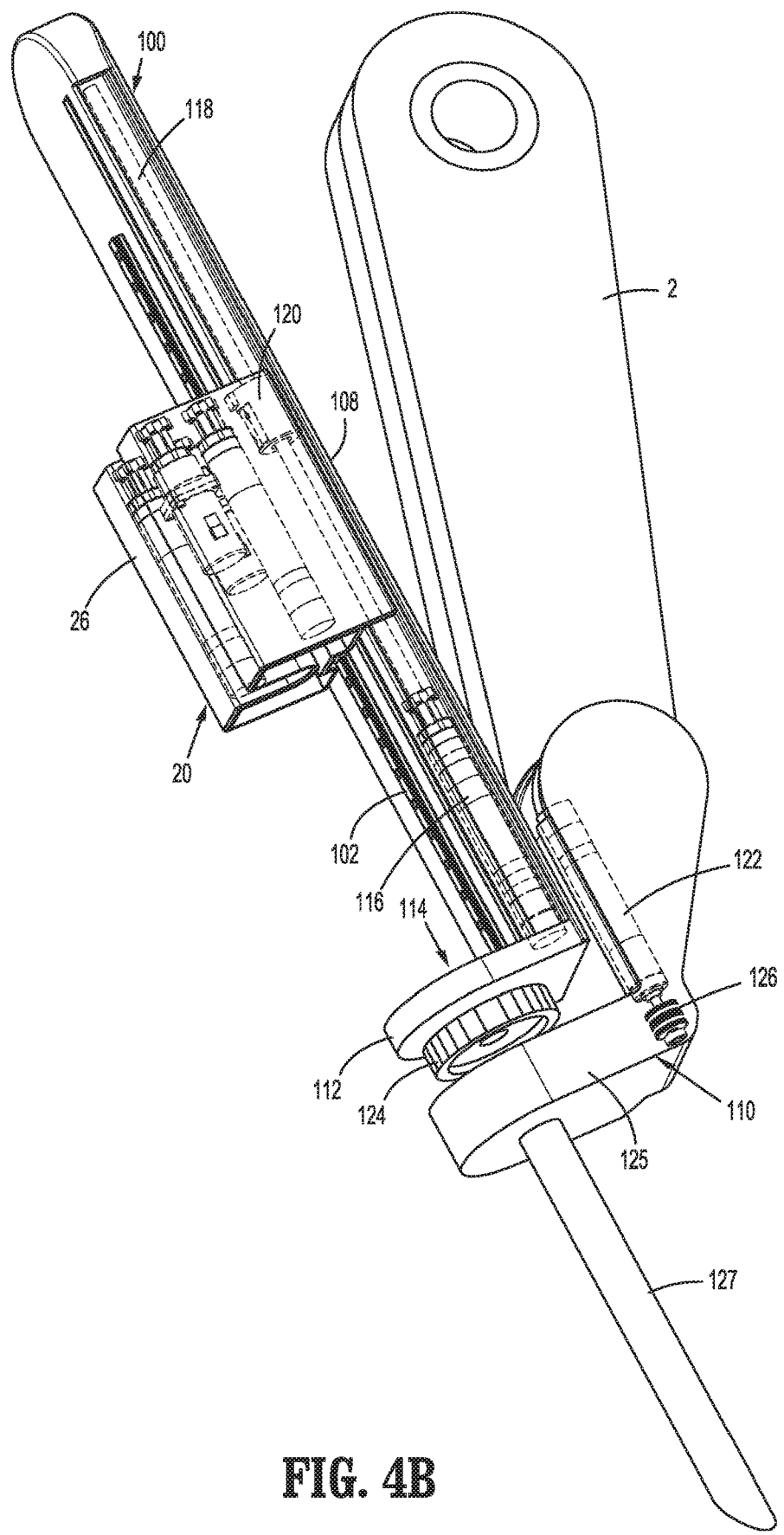
FIG. 4B is a perspective view of a second side of the slide coupled to the surgical robotic arm.
Figure 5:
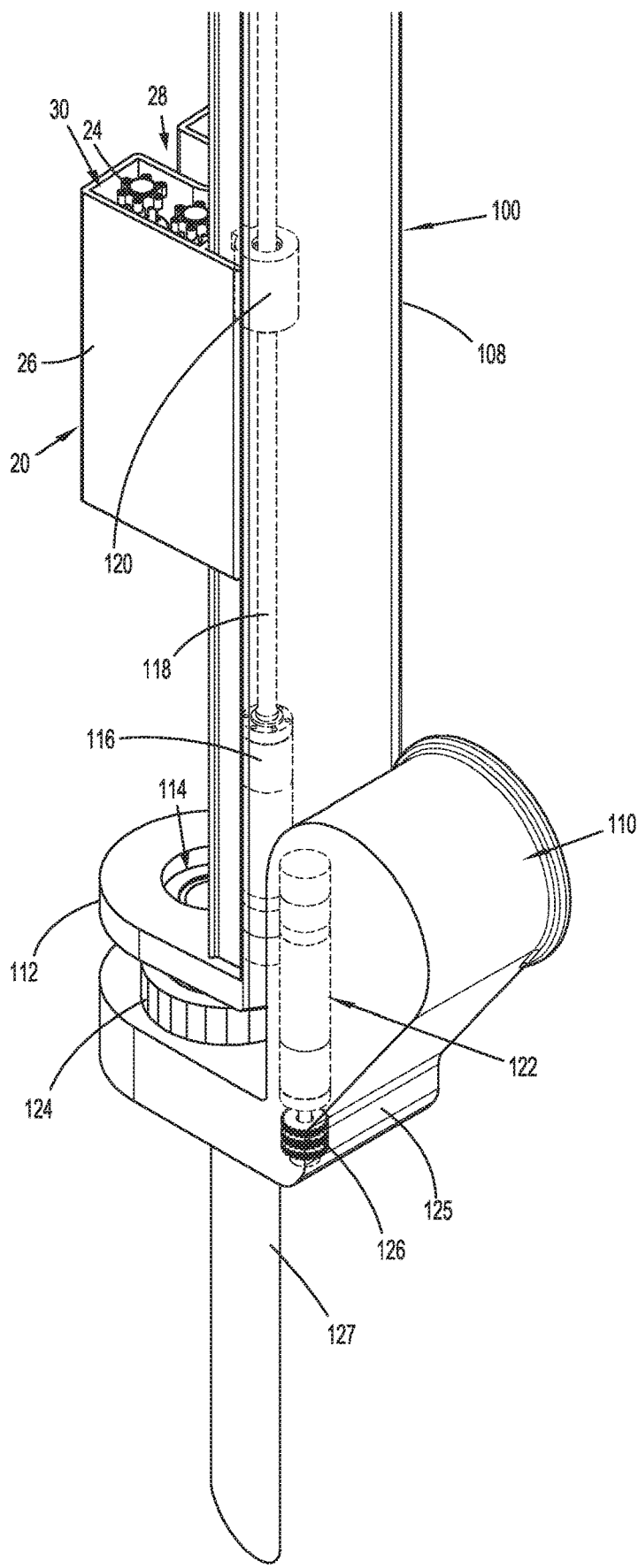
FIG. 5 is an enlarged view of the slide illustrated being supported on a coupling member.

With reference to FIGS. 4A, 4B, and 5, the surgical robotic system 1 includes a coupling member 110 rotatably attached to an end portion of the robotic arm 2 to provide an added degree of freedom for the electromechanical instrument 10. The coupling member 110 includes a main body 125 for supporting the slide 100, and a cannula 127 extending distally from the main body 125. The main body 125 may be pivotably coupled to the end portion of the robotic arm 2. The cannula 127 is dimensioned for receipt of the shaft 14 of the electromechanical instrument 10. It is contemplated that the inner diameter of the cannula 127 is large enough to permit rotation of the shaft 14 of the electromechanical instrument 10 therein. The cannula 127 is coaxial with the longitudinal axis "X" of the instrument drive unit.

The slide 100 of the surgical robotic system 1 is rotatably supported on the coupling member 110. The slide 100 includes a linear body portion 108, and an outer housing portion 112 extending perpendicularly from a distal end of the linear body portion 108. The outer housing portion 112 defines a passageway 114 therethrough dimensioned for the passage of the shaft 14 of the electromechanical instrument 10. The passageway 114 is coaxial with the cannula 127 of the coupling member 110 and the longitudinal axis "X" of the instrument drive unit 20, whereas the linear body portion 108 is offset from and parallel with the longitudinal axis "X" of the instrument drive unit and the cannula 127 of the coupling member 110.

The track 102 of the slide 100 is defined along the length of the linear body portion 108. The track 102 of the slide 100 may be a single rail or a pair of parallel rails that extend parallel to and offset from the longitudinal axis "X" of the instrument drive unit 20. As mentioned above, the housing 26 of the instrument drive unit 20 is slidably coupled to the track 102 of the slide 100.

The slide 100 supports or houses a drive motor 116 and includes a lead screw 118 operably coupled to the drive motor 116. The lead screw 118 extends along a length of the slide 100 and has a sleeve or tubular member 120 operably coupled thereto. The sleeve 120 is axially movable along the lead screw 118 and keyed to the rail 100 to prevent the sleeve 120 from rotating with the lead screw 118. The sleeve 120 is fixed to the housing 26 of the instrument drive unit 20 via bolts, screws, or the like. As such, axial translation of the sleeve 120 along the lead screw 118 causes the instrument drive unit 20 to move along the track 102 of the slide 100.

The coupling member 110 may further include an electromechanical actuator, such as, for example, a drive motor 122. The drive motor 122 is operably coupled to the slide 100 to drive a rotation of the slide 100. For example, the slide 100 may include a ring gear 124 fixed to the outer housing portion 112 thereof. The ring gear 124 is operably coupled to a gear 126 of the drive motor 122 via a timing belt (not shown) that surrounds both the ring gear 124 and the gear 126 of the drive motor 122. As such, an actuation of the drive motor 122 rotates the ring gear 124 and, in turn, rotates the slide 100 relative to the coupling member 110 about the longitudinal axis "X" of the instrument drive unit 20 (as indicated by arrow "B" of FIG. 4A). In other aspects, the slide 100 may be rotatable about its own longitudinal axis. In other embodiments, the coupling member 110 may have a motor-driven internal gear (not shown) that surrounds and operably couples with the ring gear 124 of the slide 100 for driving a rotation of the slide 100. It is contemplated that in place of the timing belt, one or more intermediate gears (not shown) may be provided to intercouple the ring gear 124 of the slide 100 and the gear 126 of the drive motor 122.

Figure 2:
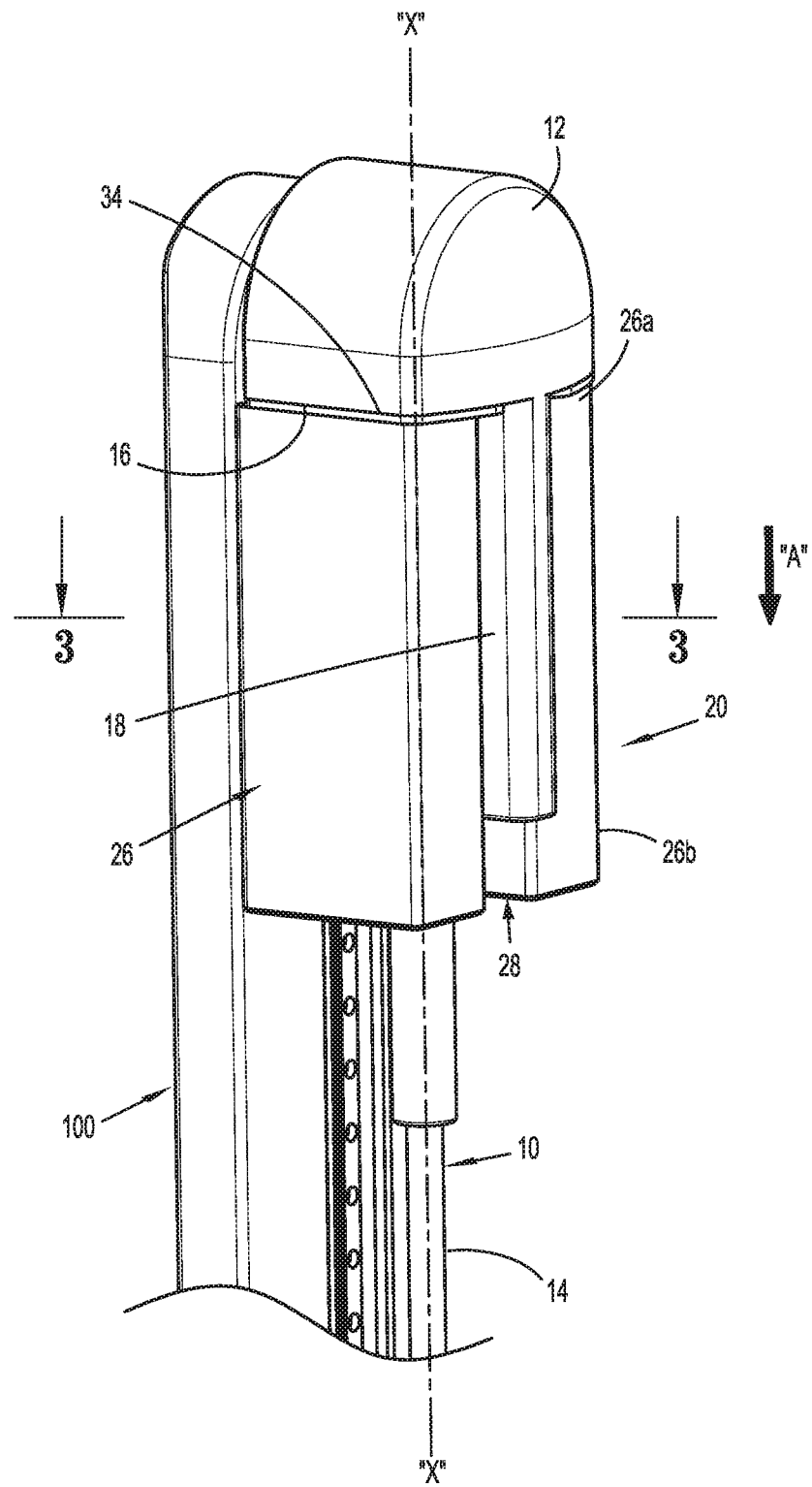
FIG. 2 is a partial perspective view of the instrument drive unit and an electromechanical instrument coupled to the slide of the surgical robotic system.

In operation, the electromechanical instrument 10 is coupled to the instrument drive unit 20 by passing the shaft 12 of the electromechanical instrument 10 through the channel 28 of the housing 26 of the instrument drive unit 20 and the cannula 127 of the coupling member 110 in a distal direction, indicated by arrow "A" in FIG. 2. The distal surface 16 of the main body portion 12 of the electromechanical instrument 10 is positioned on the proximal surface 34 of the housing 26 of the instrument drive unit 10 and the fin 18 of the electromechanical instrument 10 is received in the channel 28 of the housing 26 of the instrument drive unit 20.

With the main body portion 12 of the electromechanical instrument 10 supported on the instrument drive unit 10, the gears 24 of the drive motors 22 of the instrument drive unit 20 interface with corresponding gears/couplers (not shown) in the distal end of the main body portion 12 of the electromechanical instrument 10. It is contemplated that an actuation of one of the drive motors 22 of the instrument drive unit 20 may effect a function of the electromechanical instrument 10, such as, for example, a stapling function, an opening or closing of jaw members, the advancement of a knife, etc.

In some instances, it may be desirable or required to rotate the electromechanical instrument 10 about its longitudinal axis. To do so, the electromechanical actuator 122 of the coupling member 110 is actuated to rotate the associated gear 126. A rotation of the gear 126 drives a rotation of the slide 100 about the longitudinal axis of the instrument drive unit 20 due to the gear 126 of the coupling member 110 being operably coupled to the ring gear 124 of the slide 100. Since the instrument drive unit 20 and the electromechanical instrument 10 are both non-rotatably supported on the slide 100, the rotation of the slide 100 results in a corresponding rotation of the instrument drive unit 20 and the electromechanical instrument 10. Due to the shaft 12 of the electromechanical instrument being disposed within the cannula 127 of the coupling member 110, rotation of the slide 100 causes the shaft 12 to rotate within the cannula 127 about the longitudinal axis "X" (as indicated by arrow "B" of FIG. 4A).

In some operations, the axial position of the electromechanical instrument 10 relative to the slide 100 may be adjusted. To adjust the axial position of the electromechanical instrument 10, the drive motor 116 within the slide 100 is actuated to drive a rotation of the associated lead screw 118. A rotation of the lead screw 118 drives the sleeve 120 along the axis of the lead screw 118. Due to the sleeve 120 being fixed to the housing 26 of the instrument drive unit 20, the instrument drive unit 20 moves along the track 102 of the slide 100 as the sleeve 120 axially moves along the lead screw 118. Since the electromechanical instrument 10 is coupled to the instrument drive unit 20, the electromechanical instrument 10 moves with the instrument drive unit 20, thereby adjusting the axial position of the electromechanical instrument 10.

Figure 6:
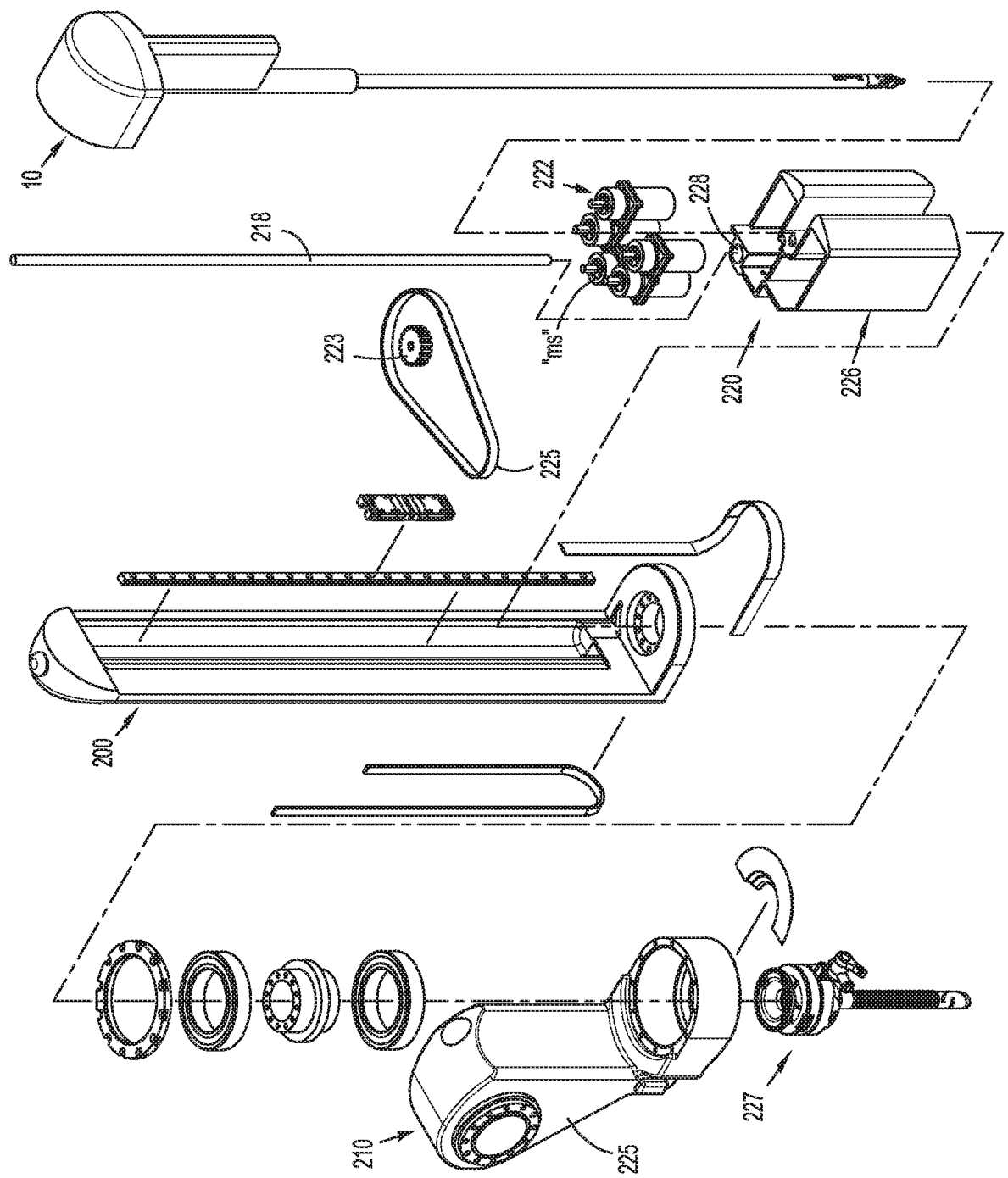
FIG. 6 is a perspective view, with parts separated, of another embodiment of a slide, a coupling member, and an instrument drive unit in accordance with the principles of the present disclosure.

With reference to FIG. 6, further embodiments of a coupling member 210, a slide 200, and an instrument drive unit 220 are shown. Due to the similarities between the coupling member 210, the slide 200, and the instrument drive 220 of the present embodiment and the respective coupling member 110, slide 100, and instrument drive unit 20 described above, only those elements of the coupling member 210, the slide 200, and the instrument drive 220 deemed necessary to elucidate the differences from the respective coupling member 110, slide 100, and instrument drive 20 described above will be described in detail.

The coupling member 210 is configured to be rotatably attached to an end portion of the robotic arm 2 (FIG. 1) to provide an added degree of freedom for an electromechanical instrument, such as, for example, the electromechanical surgical instrument 10. The coupling member 210 includes a main body 225 and a cannula 227 detachably coupled to the main body 225.

The instrument drive unit 220 includes a housing 226 and a plurality of motors 222 housed therein. The housing 226 defines a bore 228 therethrough dimensioned for receipt of a screw 218. Opposing ends of the screw 218 may be supported on or in the slide 200 and prevented from rotating relative thereto. A nut or sprocket 223 may be operably coupled (e.g., threadedly coupled) to the screw 218 and axially restrained relative to the instrument drive unit 220. A fifth drive motor "M5" may be operably coupled to the drive unit via a drive belt 225, such that an actuation of the fifth drive motor "M5" rotates the drive belt 225, which in turn, rotates the nut 223 about the screw 218. As the nut 223 rotates about the screw 218, the nut 223, along with the instrument drive unit 220, moves axially along the screw 218 to adjust the axial position of the instrument drive unit 220.

Figure 7:
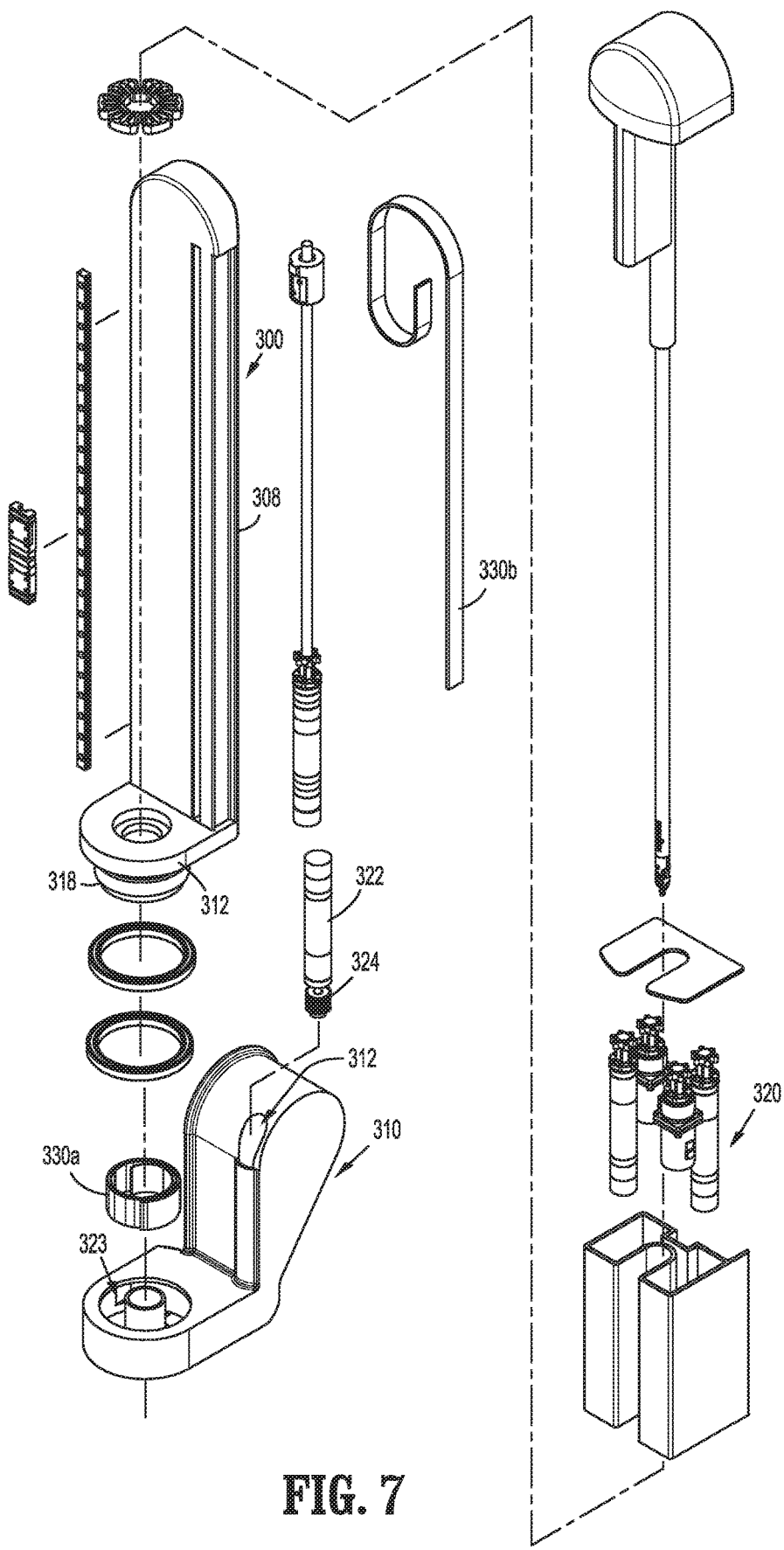
FIG. 7 is a perspective view, with parts separated, of yet another embodiment of a slide, a coupling member, and an instrument drive unit in accordance with the principles of the present disclosure.

With reference to FIG. 7, further embodiments of a coupling member 310, a slide 300, and an instrument drive unit 320 are shown. Due to the similarities between the coupling member 310, the slide 300, and the instrument drive 320 of the present embodiment and the respective coupling member 110, slide 100, and instrument drive unit 20 described above, only those elements of the coupling member 310, the slide 300, and the instrument drive 320 deemed necessary to elucidate the differences from the respective coupling member 110, slide 100, and instrument drive 20 described above will be described in detail.

The coupling member 310 defines a bore 312 therethrough dimensioned for receipt of a drive motor 322. The drive motor 322 has a gear 324 operably coupled to the slide 300, such that a rotation of the gear 324 causes the slide 300 to rotate relative to the coupling member 310. In embodiments, the motor 322 may be a through-bore motor. The slide 300 has a linear body portion 308 and an outer housing portion 312 extending laterally outward from a distal end of the linear body portion 308. The outer housing portion 312 of the slide 300 has a ring member 318 extending distally therefrom. The ring member 318 of the slide 300 is configured to be rotatably received in an annular cavity 323 defined in the coupling member 310. The ring member 318 of the slide 300 may be retained in the annular cavity 323 of the coupling member 310.

In embodiments, a first ribbon cable 330a may be received in the annular cavity 323 of the coupling member 310. The first ribbon cable may be detachably coupled to an end of a second ribbon cable 330b.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A surgical robotic system, comprising:
   a robotic arm;
   an elongated slide coupled to the robotic arm and defining a track, the elongated slide defining a longitudinal axis; and
   an instrument drive unit coupled to the track and configured to move along the track, the instrument drive unit including at least one motor configured to interface with an electromechanical instrument to actuate functions of the electromechanical instrument, wherein the slide is configured to rotate relative to the robotic arm about a longitudinal axis defined by the instrument drive unit, the longitudinal axis of the instrument drive unit being parallel with the longitudinal axis of the elongated slide.

2. The surgical robotic system according to claim 1, wherein the at least one motor has a coupler for interfacing with a corresponding coupler of the electromechanical surgical instrument, the coupler of the at least one motor being disposed adjacent a proximal end of the instrument drive unit.

3. The surgical robotic system according to claim 2, wherein the instrument drive unit further includes a housing slidably coupled to the track of the slide, the housing having the at least one motor disposed therein.

4. The surgical robotic system according to claim 3, wherein the coupler of the at least one motor is disposed within a proximal end of the housing.

5. The surgical robotic system according to claim 2, wherein the coupler of the at least one motor is a gear.

6. The surgical robotic system according to claim 1, wherein the instrument drive unit further includes a housing slidably coupled to the track of the slide, the housing having the at least one motor disposed therein.

7. The surgical robotic system according to claim 6, wherein the housing defines an elongated channel along its length, the channel dimensioned for receipt of a shaft of the electromechanical instrument.

8. The surgical robotic system according to claim 6, wherein the housing has a proximal end configured to support thereon a body portion of the electromechanical instrument.

9. The surgical robotic system according to claim 8, wherein the proximal end of the housing of the instrument drive unit is configured to non-rotatably support the electromechanical instrument.

10. The surgical robotic system according to claim 1, wherein the instrument drive unit rotates relative to the robotic arm with a rotation of the slide.

11. The surgical robotic system according to claim 1, further comprising a coupling member attached to an end portion of the robotic arm, the coupling member rotatably supporting the slide thereon.

12. The surgical robotic system according to claim 11, wherein the coupling member includes a cannula configured for receipt of a shaft of the electromechanical instrument, wherein the longitudinal axis of the instrument drive unit is coaxial with a central longitudinal axis of the cannula.

13. The surgical robotic system according to claim 1, further comprising an electro-mechanical actuator coupled to the slide and configured to rotate the slide about the longitudinal axis of the instrument drive unit.

14. The surgical robotic system according to claim 13, wherein the electro-mechanical actuator includes a drive motor and a gear driven by the drive motor, the gear being operably coupled to the slide, such that actuation of the drive motor effects a rotation of the slide.

15. A surgical robotic system, comprising:
an electromechanical instrument defining a central longitudinal axis along a length thereof and including:
a housing; and
a shaft extending distally from the housing;
an elongated slide including a track, the track defining a longitudinal axis that is parallel with the central longitudinal axis of the electromechanical instrument;
a coupling member rotatably supporting a distal end portion of the elongated slide; and
an instrument drive unit including:
a housing slidably coupled to the track of the elongated slide, the housing of the instrument drive unit having a proximal-facing surface configured to support a distal- facing surface of the housing of the electromechanical instrument; and
at least one motor disposed in the housing of the instrument drive unit and configured to interface with a driven component of the electromechanical instrument to actuate functions of the electromechanical instrument, wherein the coupling member is configured to rotate the elongated slide, the instrument drive unit, and the electromechanical instrument about the central longitudinal axis of the electromechanical instrument.

16. The surgical robotic system according to claim 15, wherein the at least one motor has a coupler for interfacing with a corresponding coupler of the electromechanical surgical instrument, the coupler of the at least one motor being disposed adjacent a proximal end of the instrument drive unit.

17. The surgical robotic system according to claim 15, wherein the housing of the instrument drive unit defines an elongated channel along its length, the channel dimensioned for receipt of the shaft of the electromechanical instrument.

18. The surgical robotic system according to claim 15, wherein the elongated slide, the instrument drive unit, and the electromechanical instrument are configured to rotate together about a rotation axis that is parallel with the longitudinal axis of the elongated slide and the central longitudinal axis of the electromechanical instrument.

19. A surgical robotic system, comprising:
an elongated slide having a track, the track defining a longitudinal axis;
a coupling member rotatably supporting a distal end portion of the elongated slide; and
an instrument drive unit coupled to the elongated slide and configured to move axially along the track, the instrument drive unit including at least one motor configured to interface with an electromechanical instrument to actuate functions of the electromechanical instrument, the instrument drive unit defining a longitudinal axis along a length thereof that is parallel with the longitudinal axis of the track of the elongated slide, wherein the coupling member is configured to rotate the elongated slide and the instrument drive unit about the longitudinal axis of the instrument drive unit.

20. The surgical robotic system according to claim 19, wherein the elongated slide and the instrument drive unit are configured to rotate together, in response to an actuation of a motor of the coupling member, about a rotation axis that is parallel with the longitudinal axis of the instrument drive unit and the longitudinal axis of the track of the elongated slide.

* * * * *